United States Patent [19]

Isono et al.

[11] Patent Number: 5,322,854

[45] Date of Patent: Jun. 21, 1994

[54] REVEROMYCIN A, METHOD FOR PREPARING THE SAME, AND ANTITUMOR AGENT AND ANTIFUNGAL AGENT COMPRISING THE SAME

[75] Inventors: Kiyoshi Isono; Hiroyuki Osada, both of Wako; Hidetoshi Takahashi, Tochigi; Gosei Kawanishi, Ichikawa, all of Japan

[73] Assignees: Rikagaku Kenkyusho, Wako; Snow Brand Milk Products Co., Ltd., Sapporo, both of Japan

[21] Appl. No.: 828,851

[22] PCT Filed: Jun. 7, 1991

[86] PCT No.: PCT/JP91/00772

§ 371 Date: Feb. 6, 1992

§ 102(e) Date: Feb. 6, 1992

[87] PCT Pub. No.: WO91/19718

PCT Pub. Date: Dec. 26, 1991

[30] Foreign Application Priority Data

Jun. 14, 1990 [JP] Japan .................. 2-155816

[51] Int. Cl.$^5$ ............................. A61K 31/35
[52] U.S. Cl. ..................... 514/451; 549/343
[58] Field of Search .............. 549/343; 514/460, 451

[56] References Cited

FOREIGN PATENT DOCUMENTS 32184 1/1991 Japan .

OTHER PUBLICATIONS

J. H. Antibiotics, vol. 44, No. 2 pp. 259–261 Feb. 1991 H. Osada et al "Reveromycin A, A new antibiotic which inhibits the mitogenic activity of epidermal growth factor".

Primary Examiner—C. Warren Ivy
Assistant Examiner—A. Owens
Attorney, Agent, or Firm—Oblon, Spivak, McClelland, Maier & Neustadt

[57] ABSTRACT

A novel antibiotic Reveromycin A represented by the following formula:

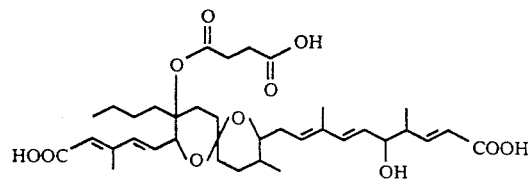

and a process for preparing said antibiotic which comprises the steps of cultivating a strain which belongs to genus Streptomyces and produces the antibiotic Reveromycin A, and recovering the antibiotic Reveromycin A from the culture product are provided. The antibiotic is useful for its anti-leukemia and antifungal activities.

3 Claims, 4 Drawing Sheets

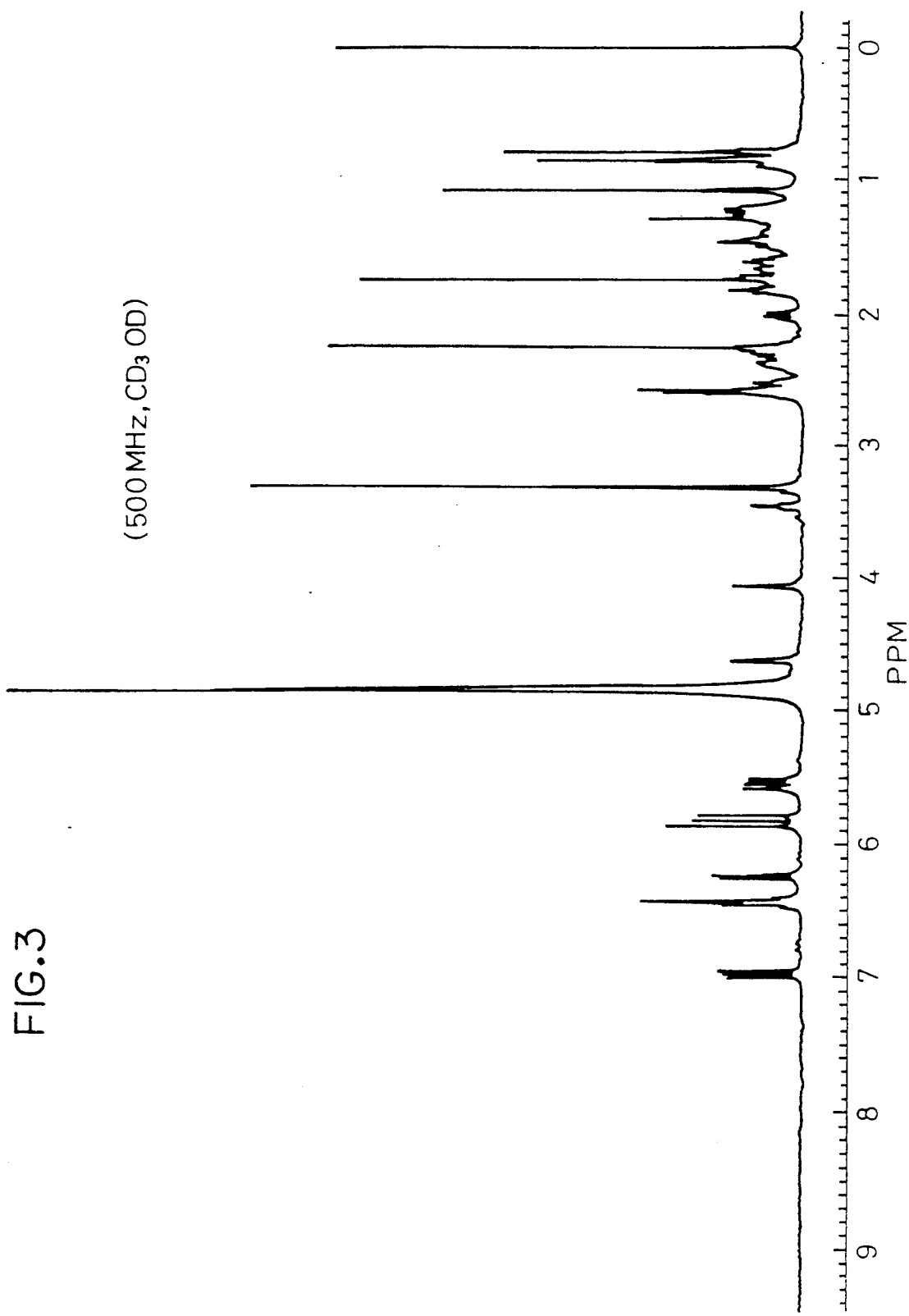
FIG.3 (500 MHz, CD₃OD)

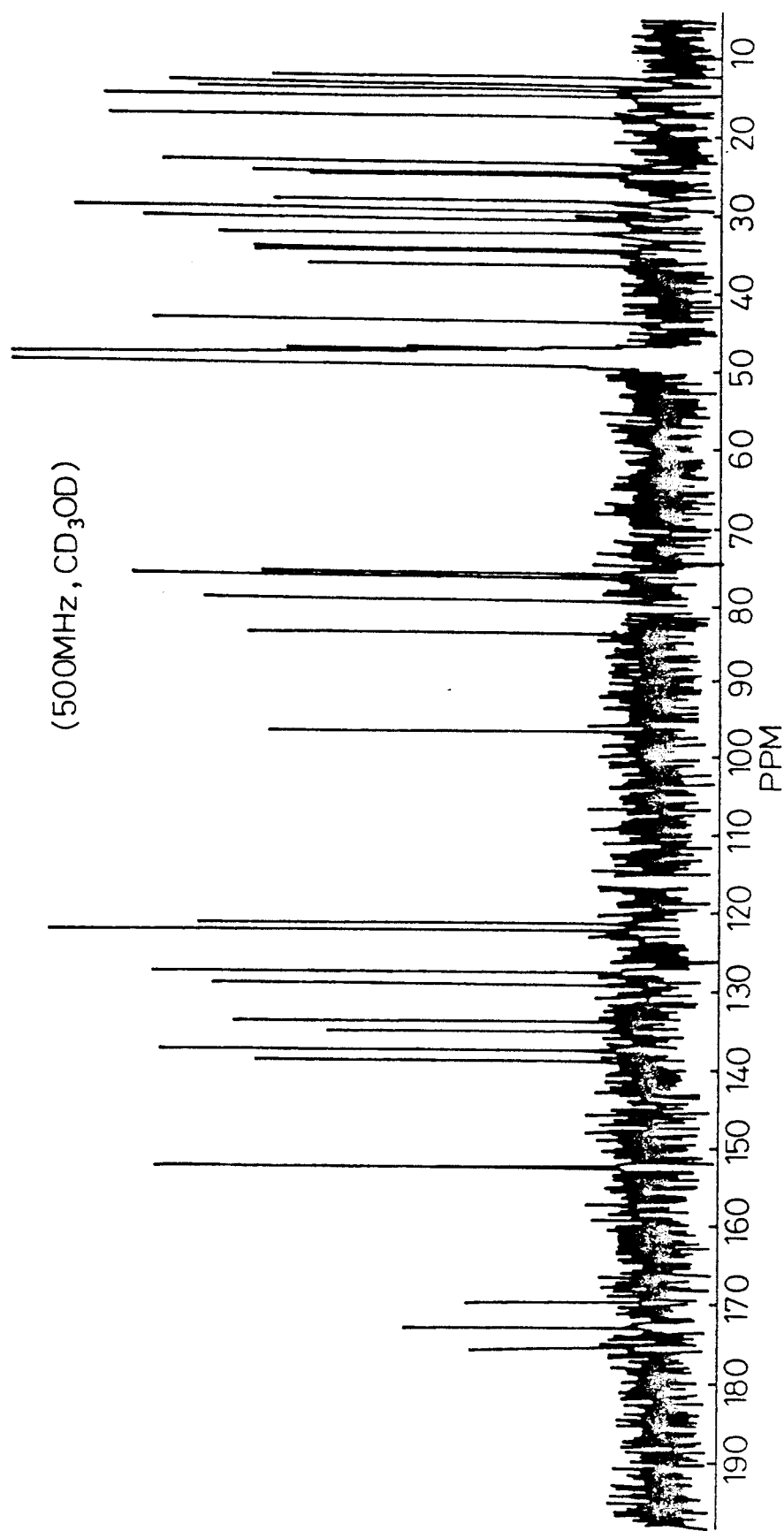
FIG.4 (500MHz, CD₃OD)

REVEROMYCIN A, METHOD FOR PREPARING THE SAME, AND ANTITUMOR AGENT AND ANTIFUNGAL AGENT COMPRISING THE SAME

TECHNICAL FIELD

The present invention relates to a novel antibiotic, a method for preparing the same, and an antitumor agent and an antifungal agent comprising the antibiotic as an effective ingredient.

BACKGROUND ART

The main cause of the abnormal growth of cancer cells is the dysfunction of the signal transduction system for cell growth factors. For example, various types of tumor cells have been found to secrete tumor growth factor alpha (TGF-α) which enhances the autoproliferation of the tumor cells. An agent which can selectively inhibit the action of TGF-α can thus be expected to be useful as an anticancer agent.

Erbstatin and other agents of this sort are known. However, they are not sufficiently potent and, moreover, are not clinically useful because they lose their effects in blood.

Accordingly, an object of the present invention is to provide a novel substance which inhibits the action of tumor growth factors and inhibits the growth of tumor cells. Another object of the present invention is to provide an antitumor agent comprising the substance.

The inventors of the present invention screened various inhibitors using Epidermal growth factor (EGF), a cell growth factor similar to TGF-α. As a result, the inventors found that a novel substance, Reveromycin A, has potent inhibitory activity against EGF and inhibits the growth of various kinds of tumor cells. The present invention was achieved on the basis of this findings.

Furthermore, the inventors also found that Reveromycin A has antimicrobial activity against fungi and that a pharmaceutical composition comprising this substance is useful as an antifungal agent for achieving the present invention.

DISCLOSURE OF THE INVENTION

The present invention provides a novel antibiotic Reveromycin A, and a process for preparing the antibiotic Reveromycin A which comprises the steps of cultivating a strain which belongs to Streptomyces and produces the antibiotic Reveromycin A, and separating the antibiotic Reveromycin A from the cultured product. The Reveromycin A of the present invention has antitumor and antifungal activity. In accordance with other of its features, the present invention provides an antitumor agent comprising the antibiotic Reveromycin A as an effective ingredient, and an antifungal agent comprising the antibiotic Reveromycin A as an effective ingredient.

BRIEF DESCRIPTION OF DRAWINGS

FIG. 3 shows the 500 MHz $^1$H NMR spectrum (CD$_3$OD) of the antibiotic Reveromycin A.

FIG. 4 shows the 500 MHz $^{13}$C NMR spectrum (CD$_3$OD) of the antibiotic Reveromycin A.

BEST MODE FOR CARRYING OUT THE INVENTION

Figure 1:
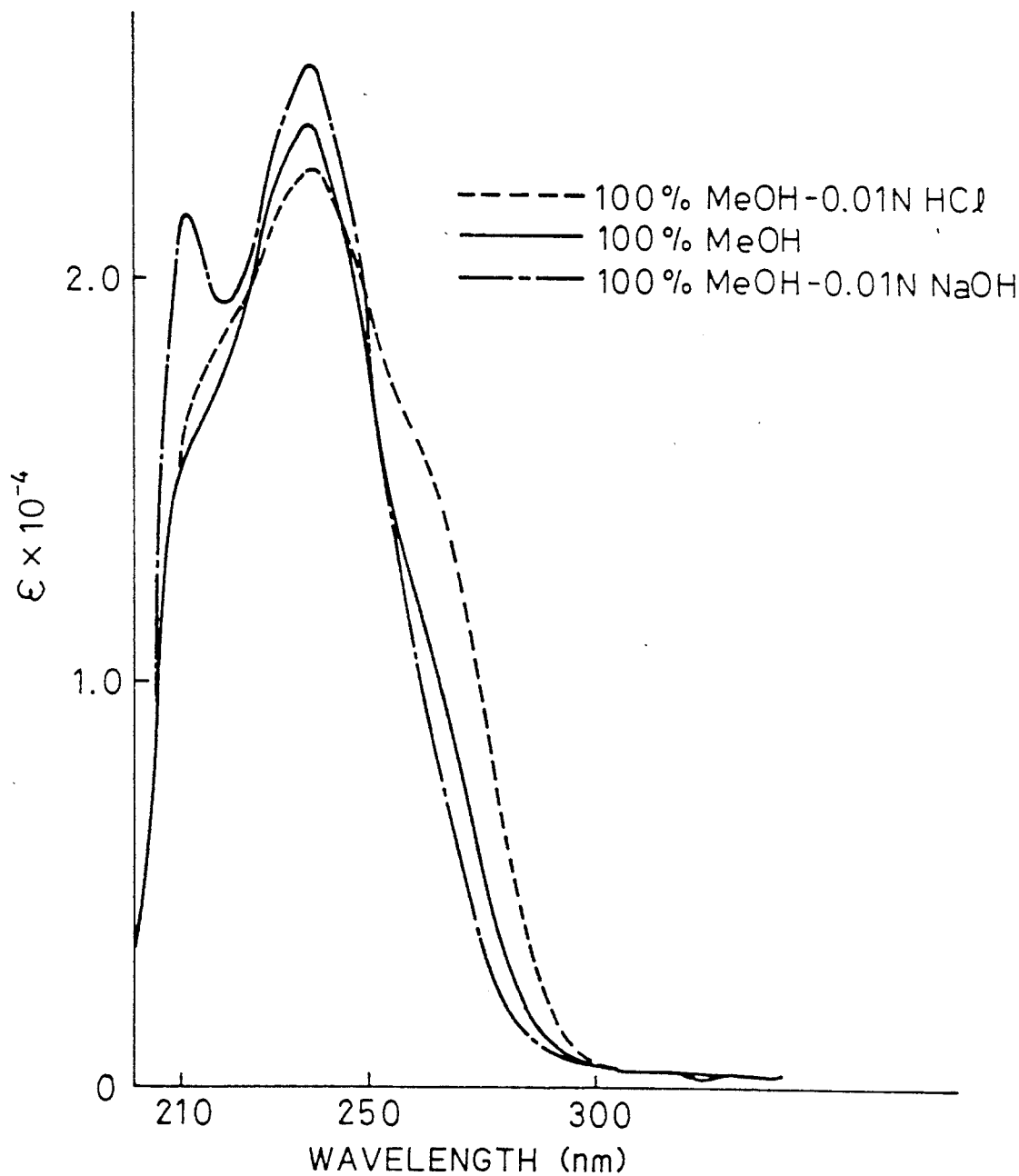
FIG. 1 shows the ultraviolet absorption spectra of the antibiotic Reveromycin A of the present invention, in which —represents the spectrum measured in 100% methanol; —represents the spectrum measured in methanol/0.01N HCl; and · represents the spectrum measured in methanol/0.01N NaOH.
Figure 2:
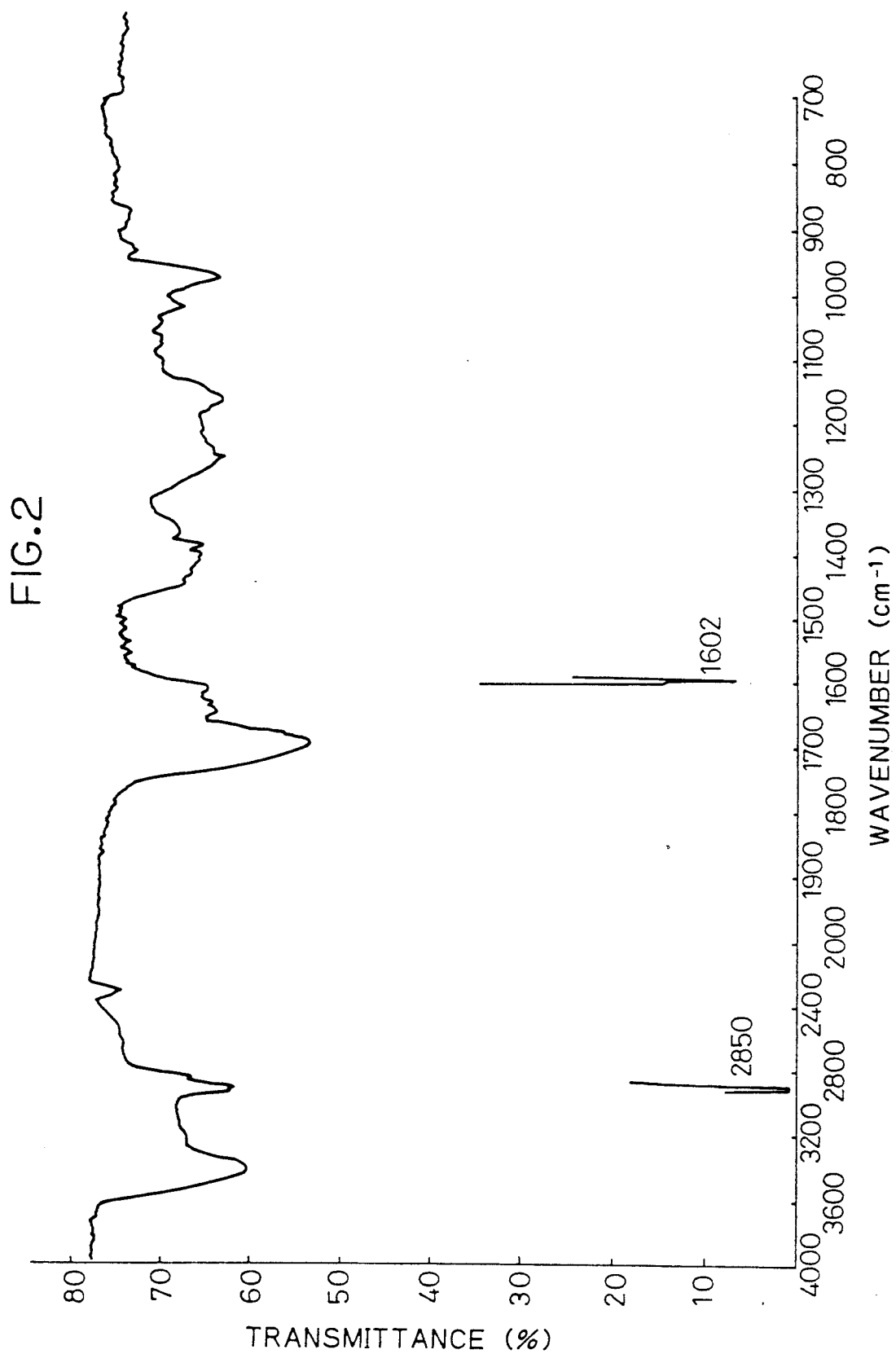
FIG. 2 shows the infrared absorption spectrum (KBr) of the antibiotic Reveromycin A.

The antibiotic Reveromycin A of the present invention is a novel antibiotic represented by the following formula:

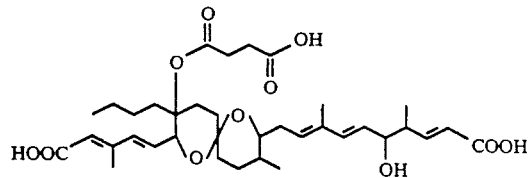

which has the physicochemical properties described below.

Physicochemical properties of the antibiotic Reveromycin A:

(1) Appearance: white powder;
(2) Melting Point: 95° C.;
(3) Molecular Formula: $C_{36}H_{52}O_{11}$;
(4) Elemental Analysis: C 64.45%; H 8.06% ($C_{36}H_{52}O_{11} \cdot \frac{1}{2} H_2O$);
(5) Specific Rotation: $[\alpha]^{20}_D = -115°$ (c=0.1, methanol);
(6) Ultra-Violet Absorption Spectrum (methanol): $\lambda^{MeOH}_{max}$ nm (ε)=238(25,300) and 260(sh, 12,200);
(7) Infra-Red Absorption Spectrum (KBr): 3430, 2930, 1690, 1640, 1610, 1380, 1250, 1160, and 970 cm$^{-1}$;
(8) Solubility: easily soluble in dimethylsulfoxide, ethyl acetate, and methanol and insoluble in aqueous acidic solution;
(9) High Resolution FAB-MS: 683.3496 (M+Na)$^+$; and
(10) Color Reaction: positive by iodide, anisaldehyde, and BCG; and negative in ninhydrine and Dragenforff's reagent.

The antibiotic Reveromycin A was isolated from the culture product obtained by cultivating Streptomyces sp. SN-593 which was isolated from soil collected in Kurafuchi Village, Gumma Prefecture, Japan. This strain Streptomyces sp. SN-593 has been deposited at the Fermentation Research Institute, Agency of Industrial Science and Technology (1-1-3, Higashi Tsukuba, Ibaraki 305, Japan) under the access number FERM P-11503 which was amended to the access number BP-3406 under the Budapest Treaty on May 20, 1991.

Streptomyces sp. SN-593 exhibits the following bacteriological characteristics:

1. L,L-Diaminopimelic acid is observed on a thin layer chromatogram after the cells are hydrolyzed by 6N HCl at 110° C. for 18 hours. Meso-diaminopimelic acid is not observed. When the strain is cultured on an agarose plate and examined with an electron microscope, incomplete spiral aerial hyphae are observed and the surface of the cylindrical conidium is smooth.

2. Cultural characteristics on various media are as follows (Cultured for 20 days at 27° C. Colors are indicated according to the 4th edition of Color Harmony Manual, Container Co., Ltd.):

1) Starch-yeast agar

Growth: good
Aerial hyphae: rich
Color of aerial hyphae: gray (2ih)
Color of undersurface: beaver (3li)
Soluble pigment: not observed.
2) Yeast extract-molt extract agar
Growth: good
Aerial hyphae: rich
Color of aerial hyphae: gray (3ih)
Color of undersurface: chocolate (5po)
Soluble pigment: not observed.
3) Oatmeal agar
Growth: good
Aerial hyphae: rich
Color of aerial hyphae: 2 ml
Color of undersurface: mustard (2ne)
Soluble pigment: not observed.
4) Starch-inorganic salt agar
Growth: good
Aerial hyphae: rich
Color of aerial hyphae: gray (3ih)
Color of undersurface: chestnut brown (4ni)
Soluble pigment: not observed.
5) V8 juice agar
Growth: medium
Aerial hyphae: poor
Color of aerial hyphae: gray (3ih)
Color of undersurface: black (2po)
Soluble pigment: not observed.
6) Sucrose-nitrate agar
Growth: medium
Aerial hyphae: good
Color of aerial hyphae: yellowish brown (2ge)
Color of undersurface: colorless
Soluble pigment: not observed.
7) Glucose-asparagine agar
Growth: fairly good
Aerial hyphae: good
Color of aerial hyphae: gray (2fe)
Color of undersurface: mustard (2ne)
Soluble pigment: not observed.
8) Glycerol-asparagine agar
Growth: medium
Aerial hyphae: medium
Color of aerial hyphae: natural (2dc)
Color of undersurface: yellow (3ng)
Soluble pigment: not observed.
9) Potato-carrot agar
Growth: fairly good
Aerial hyphae: good
Color of aerial hyphae: gray (5fe)
Color of undersurface: colorless
Soluble pigment: not observed.

From the foregoing bacterial characteristics, it was concluded that the strain SN-593 belongs to the genus Streptomyces.

The antibiotic Reveromycin A can be prepared by inoculating the above-described strain into a medium containing assimilable nutrients, and cultivating the medium under an aerial condition. It is to be understood that strains producing the antibiotic Reveromycin A are not limited to the strain described above, and that any strain can be used in the present invention so far as it belongs to genus Streptomyces and is able to produce the antibiotic Reveromycin A.

The cultivation of the above-described microorganisms can be conducted basically according to cultivation methods generally used for microorganisms. Ordinarily it is preferable to use liquid cultivation involving shaking culture or aerial spinner culture under an aerial condition.

The medium used for the cultivation need only be one containing assimilable nutrients available to Streptomyces. Any type of medium such as a synthetic medium, a semi-synthetic medium, or an agar medium may be used. As the source of carbon, the medium may contain glucose, sucrose, fructose, glycerol, dextrin, starch, molasses, corn steep liquor, organic acids, or mixtures thereof. Examples of the source of nitrogen include organic nitrogen sources such as pharmamedia, peptone, meat extract, yeast extract, soybean meal, casein, amino acids, and urea; and inorganic nitrogen sources such as sodium nitrate and ammonium sulfate, which may be used alone or in combination.

If desired, sodium salts, potassium salts, magnesium salts, phosphates, or other heavy metal salts may be added. Furthermore, where significant foaming occurs during the cultivation, various kinds of known defoaming agent such as Adecanol (trade name) or silicone oil may suitably be added to the medium. However, the amount added should be kept within the range that does not affect the production of the desired compound. For example, the deforming agent should preferably be added and used at a concentration of not more than 0.5% by weight.

The pH of the culture medium is preferably within the optimum pH range for the strain used, which is generally around neutral. The temperature of the medium should be within the range that is suitable for good growth of the strain used, which is generally between 2.0 and 40° C. and most preferably at about 27° C. The cultivation time should generally be about one to five days, preferably about 72 hours. The desired antibiotic Reveromycin A can be produced and accumulated in the medium by the cultivation described above. The conditions for the cultivation herein described may suitably altered depending on the type or characteristics of the microorganism used or other outside conditions. It will be understood that a person of ordinary skill in the art can readily select or control the optimum conditions for the cultivation.

The isolation of the antibiotic Reveromycin A produced by the above-described cultivation may be conducted by a commonly used method for recovering fermentation products at the time when the accumulated amount of the antibiotic becomes maximum. For example, the isolation may be conducted by processes utilizing difference in solubility, difference in adsorbing affinity, or difference in molecular weight between Reveromycin A and impurities. These processes can be used singly, in suitable combination, or repeatedly.

Specifically, Reveromycin A, which accumulates mostly in the cultured medium, can be extracted in a fraction together with other active substances by purifying the filtrate of the culture medium by a combination of various kinds of gel filtration chromatography, adsorption chromatography, and liquid chromatography. Purified Reveromycin A can be obtained as white powder by applying the powder product obtained by lyophilizing the fraction described above to a high performance liquid chromatography (using a capsule pack column, for example) and purifying the product by using an eluent containing 18% methanol/0.01% ammonia.

One of best embodiments of preparation of the antibiotic Reveromycin A of the present invention is described below. It should be understood, however, that the process for preparing the antibiotic Reveromycin A of the present invention is not limited to this example.

EXAMPLE 1

Streptomyces SN-593 was inoculated into 18 liters of medium comprising 2% glucose; 1% soluble starch; 0.1% meat extract; 0.4% dried yeast; 2.5% soybean meal; and 0.2% sodium chloride, and the medium was subjected to aerial stirring cultivation at 27° C. for 72 hours. The filtrate of the total culture medium was adjusted to pH 10 and extracted with an equal volume of ethyl acetate. The aqueous layer was adjusted to pH 5 and further extracted with an equal volume of ethyl acetate, and then, the ethyl acetate layer was concentrated under a reduced pressure to give a crude active product. The crude active product was subjected to silica gel chromatography, and after the column had been washed with chloroform/methanol (10/1 and 2/1), an active fraction was eluted with 100% methanol. The active fraction was further applied to MIC gel and eluted with 70% methanol. Then, the eluted fraction was applied to a Sephadex LH-20 column and eluted with 20% methanol to recover the active fraction, which was further developed by using a Sephadex LH-20 column under the same conditions to obtain the fraction containing Reveromycin A as the major component. The final purification was carried out by subjecting the fraction to high performance liquid chromatography (column: CAPCELL PAK $C_{18}$, 20 mm $\phi \times 250$ mm) and collecting fractions repeatedly using methanol/0.01% $NH_4OH$ as an eluent to obtain the fraction containing Reveromycin A as the single component. This fraction containing Reveromycin A was concentrated under a reduced pressure, and the remaining aqueous solution was extracted with an equal volume of ethyl acetate after being adjusted to pH 5. The ethyl acetate layer was concentrated under a reduce pressure, and the resulting residue was lyophilized to afford about 100 mg of Reveromycin A as a final white powdery product.

EXAMPLE 2

The following Table 1 shows the minimum inhibitory concentrations of the antibiotic Reveromycin A, obtained by the method described above, against various kinds of bacteria.

TABLE 1

Minimum inhibitory concentration of the antibiotic Reveromycin A against various bacteria

| Strain | MIC (μg/ml) |
| --- | --- |
| Escherichia coli JE1011 | >250 |
| Salmonella typhimurium TV119 | >250 |
| Staphylococcus aureus FPA109P | >250 |
| Xanthomonas campestris pv citri | >250 |
| Botryotinia fuckeliana IFO5365 | 16 |
| Pyricularia oryzae IFO5994 | 32 |
| Alternaria mali IFO8984 | 64 |
| Candida albicans IFO1594 | 250 |

The above-mentioned antibiotic Reveromycin A has inhibitory activity against the growth of tumor cells and antifungal activity, and thus, a composition comprising Reveromycin A is useful as an antitumor agent and an antifungal agent.

EXAMPLE 3

Experiments on the Inhibitory Activity of the Antibiotic Reveromycin Against the Growth of Tumor Cells Human leukemia cells K-562 and HL-60 were cultured in RPMI 1640 medium containing 10% fetal calf serum. Several series of diluted Reveromycin A were added to the cultured medium. After the medium was cultured for 17 hours, MTT reagent was added to the medium and the cell growth was examined. The results are summarized in Table 2.

TABLE 2

Inhibitory effect of the antibiotic Reveromycin A on cell growth (minimum inhibitory concentration)

| Cell | MIC (μg/ml) |
| --- | --- |
| Human chronic myelocytic leukemia cell K-562 | 5 |
| Human promyelocytic leukemia cell HL-60 | 1.7 |

EXAMPLE 4

Experiments of the Inhibition of DNA Synthesis in Mouse Epithelial Cells Stimulated by Epidermal Growth Factor, EGF EGF (5 ng/ml) and Reveromycin A were added to a culture of mouse epithelial cells in resting stage, and after 17 hours, $^3$H-labeled thymidine (1 μ Ci/ml) was added to the medium. The radioactivity of the acid insoluble fraction of the cells, which were labeled for 5 hours, was measured by a liquid scintillation counter to determine the amount of DNA synthesis. The ratio of inhibition was calculated by the equation set out below. The results are summarized in Table 3.

Ratio of inhibition (%) × 1/100 = 1 −

$$\frac{\text{Amount of DNA synthesis of the cell in the presence of EGF and drug} - \text{Amount of DNA synthesis of the non-treated cell}}{\text{Amount of DNA synthesis of the cell in the presence of EGF} - \text{Amount of DNA synthesis of the non-treated cell}}$$

TABLE 3

| Compound | Conc. (μg/ml) | inhibitory ratio (%) | cell toxicity |
| --- | --- | --- | --- |
| Reveromycin A | 50 | 99 | observed |
| Reveromycin A | 17 | 90 | not observed |
| Reveromycin A | 5 | 88 | not observed |
| Reveromycin A | 1.7 | 48 | not observed |
| Reveromycin A | 0.5 | 15 | not observed |

EXAMPLE 5

Effect on Rat Kidney Cell (NRK) Transformed with Temperature Sensitive Oncogene, $src^{ts}$ When $src^{ts}$-NRK cells are cultured at 32° C., spherical transformant cells can be grown. On the other hand, when they are cultured at 39° C., the spherical cells will disappear and only flat adhesive cells can be grown. Reveromycin A was added to the cultured cells at 32° C. and the cells were observed microscopically to count the number of spherical cells. The effectiveness was calculated by the equation set out below. The results are summarized in Table 4.

Ratio of inhibition × 1/100 =

$$1 - \frac{\text{Number of spherical cells observed per field after the cells were cultured at 32° C. in the presence of Reveromycin A}}{\text{Number of spherical cells observed per field after the cells were cultured at 32° C. in the absence of drug}}$$

TABLE 4

| Compound | Conc. (μg/ml) | inhibitory ratio (%) | cell toxicity |
| --- | --- | --- | --- |
| Reveromycin A | 50 | 95 | observed |
| Reveromycin A | 17 | 95 | not observed |
| Reveromycin A | 5 | 95 | not observed |
| Reveromycin A | 1.7 | 60 | not observed |
| Reveromycin A | 0.5 | 45 | not observed |

The above-described antibiotic Reveromycin A may be formulated in a pharmaceutical composition in the form of, for example, tablet, powder, capsule, injection, inhalant, or external preparation by ordinary methods, and may be administered orally or parenterally as an antitumor agent or an antifungal agent. The daily dose of the pharmaceutical composition for an adult patient is 1 to 1,000 mg as an antitumor agent or 10 to 1,000 mg as an antifungal agent, which may be increased or decreased depending on the condition of the patient or the route of administration. The acute toxicity of the antibiotic Reveromycin A is not less than 100 mg/Kg (mouse, iv.v.).

INDUSTRIAL APPLICABILITY

The antibiotic Reveromycin A has antitumor activity and antifungal activity as herein described, and thus, a pharmaceutical composition comprising the antibiotic Reveromycin A is useful as an antitumor agent and an antifungal agent.

We claim:

1. Antibiotic Reveromycin A represented by the following formula:

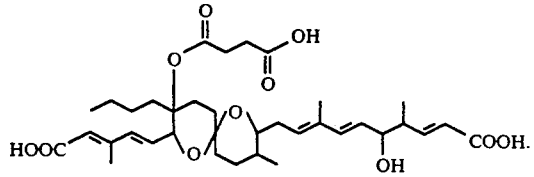

2. An anti-leukemia agent comprising an effective amount of the antibiotic Reveromycin A according to claim 1.

3. An antifungal agent comprising an effective amount of the antibiotic Reveromycin A according to claim 1.

* * * * *